United States Patent [19]
Mackles et al.

[11] Patent Number: 5,833,963
[45] Date of Patent: Nov. 10, 1998

[54] NON-TACKY AND QUICK-DRYING AQUEOUS-BASED ANTIPERSPIRANT COMPOSITIONS

[75] Inventors: Leonard Mackles, New York; Mary T. Larkin, South Salem, both of N.Y.; Lise Jorgensen, Trumbull, Conn.; Leonard Chavkin, Bloomsbury, N.J.

[73] Assignee: Bristol-Myers Squibb Company, New York, N.Y.

[21] Appl. No.: 700,165

[22] Filed: Aug. 20, 1996

[51] Int. Cl.[6] .............................. A61K 7/32; A61K 7/34; A61K 7/38; A61K 7/00
[52] U.S. Cl. ................................ 424/65; 424/66; 424/68; 424/400; 424/401
[58] Field of Search .................... 424/65, 66, 68, 424/400, 401

[56] References Cited

U.S. PATENT DOCUMENTS 5,376,363  12/1994  Benfatto et al. ......................... 424/66
5,500,209   3/1996  Ross et al. ............................... 424/66

*Primary Examiner*—Shelley A. Dodson
*Attorney, Agent, or Firm*—Charles J. Zeller

[57] ABSTRACT

The invention provides fully aqueous-based antiperspirant compositions for application onto the skin for reducing or inhibiting body malodor and perspiration. The compositions contain blocked polyglycols which function as detackifiers and/or emollients, and which provide a completely soluble environment for the antiperspirant active ingredient. The compositions of the invention are stable, are easily and inexpensively prepared and manufactured, and provide versatile formulations which may be delivered and applied to the skin by a variety of means, including roll-ons, aerosols, and the like. Without the need for emulsions or stringent alcohol additives, the aqueous-based antiperspirant solution technology of the invention provides compositions that are clear, non-tacky, quick drying, and leave little to no visible residue or film on the skin following application.

26 Claims, No Drawings

NON-TACKY AND QUICK-DRYING AQUEOUS-BASED ANTIPERSPIRANT COMPOSITIONS

FIELD OF THE INVENTION

The present invention relates generally to the field of antiperspirants and deodorants to reduce and prevent perspiration and body malodor associated with human perspiration, particularly underarm malodor, without the disadvantageous effects of stickiness or wetness following application.

BACKGROUND OF THE INVENTION

Antiperspirants combat axillary body malodors by inhibiting perspiration through the action of astringent salts such as aluminum and zirconium salts. As has been experienced by a considerable number of antiperspirant users, such active salts may be irritating and painful to the sensitive skin or body surface to which the antiperspirant is applied. Deodorants, on the other hand, prevent objectionable odors resulting from the degradation of the components of sweat which are attacked by chemicals and microbes, thereby producing foul-smelling fatty acids. Because deodorants do not inhibit sweat, but rather inhibit the growth of microorganisms that cause malodor, deodorants are generally less irritating to the skin than antiperspirants. However, the action of antiperspirants reduces or prevents wetness and sweating; therefore, antiperspirants are frequently preferred over deodorants.

In order to be effective underarm sweat inhibitors, antiperspirant salts, which comprise antiperspirants, must be used in high concentrations in products. These water-soluble salts, in concentrated solutions, are astringent when applied to the skin, and are sticky as they dry, thereby producing an unpleasant tacky feeling in the underarms. A variety of product forms have been developed with the sole purpose of dealing with this elegance problem. Originally, squeeze bottle sprays were sold, but these were wet and drippy and did little to reduce tackiness in the underarms. Creams were less sticky, but required hand application and left unsightly residues on skin and clothing. Emulsion roll-on lotions were an improvement, because they were applied directly and delivered a thin film of product, but they were still sticky, messy, and slow drying. Moreover, aerosol sprays seemed to provide an elegant product form, but they delivered a choking, dusty spray around the user's face and later on were rejected because of the negative environmental impact of their properties.

Stickiness was eliminated by the development of suspensions of antiperspirant salts, either in a volatile silicone liquid vehicle applied as a roll-on, or in a solid fatty stick that could be rubbed into the underarm area. These forms still have some significant degree of consumer acceptance, but they are being rejected by many consumers, particularly women, because of the white, powdery residue that both forms and deposits in the underarm area. This factor is particularly objectionable, since the residue is easily transferred from the underarm and is applied to and visible on the user's clothing while the user is dressing.

The high level of popularity of clear antiperspirant forms attests to the importance of the above-mentioned inelegant and negative effects in the minds of consumers. However, the development of clear antiperspirant products that are aesthetically pleasant has also eluded the formulator. Current clear products utilize solvents, cosolvents, and emollients that actually increase the stickiness of solutions of antiperspirant salts. Those that are commonly used are water-soluble glycols, such as glycerin, propylene glycol, and sorbitol, or solvents like ethanol, all of which result in products that are very sticky and tacky in the underarms, and many of which leave objectionable white residues as they dry.

In addition, a number of antiperspirants formulated as viscous, high internal phase emulsions or microemulsions and comprising oil in water compositions and various additives may show a white residue after application of the antiperspirant and drying. Such a residue may be attributed to the volatilization of the liquid component, which is usually ethanol at high levels, and the leaving behind of a film of the non-volatile powdering ingredients. Another problem in the art, especially with those antiperspirant compositions having a significantly high alcohol content, is a stinging sensation which occurs after application of the product onto the skin, particularly after shaving.

Clear or translucent gelled antiperspirant sticks which are substantially anhydrous, contain active antiperspirant material, a stabilizer as an essential component, and are gelled in a gelling agent, such as dibenzylidene monosorbitol acetal, have been disclosed (U.S. Pat. No. 5,376,363 to A. J. Benfatto et al.). However, acetal gelling agents are often unstable in the acidic environment of most antiperspirant active materials, so that suitable buffering or stabilizing agents must be discovered and used to slow down the acid attack on the gelling agent. In addition, many of the clear or translucent antiperspirant sticks containing acetal gelling agent and solubilized active antiperspirant material have the disadvantage of being inherently tacky. To further complicate the problems in the art, acid hydrolysis of the conventionally used gelling agent occurs more rapidly in aqueous solutions, so that those in the art have had to use non-aqueous formulations. Other compositions provide antiperspirant active materials in gellants of different types, such as polyamide gelling agent (U.S. Pat. No. 5,500,209 to M. S. Mendolia et al.).

Accordingly, a desired goal in the art remains for the development of clear, stable antiperspirant products which provide the following advantageous characteristics: 1) they do not feel objectionably wet or cold upon application; 2) they dry rapidly; 3) they do not feel sticky or tacky; and 4) they leave no visible residue in the underarm area after application.

The present invention provides fully soluble, aqueous-based antiperspirant compositions that can be formulated in all types of liquid dosage or delivery forms. The antiperspirant compositions or formulations of the invention comprise newly-discovered classes of emollient solvents that are stable, safe for application to human skin, and uniquely meet the criteria as set forth above. The present compositions provide clear, cosmetically elegant antiperspirant formulations that are aesthetically acceptable after application, are non-irritating to the body and skin of the user, and are capable of effectively inhibiting perspiration and preventing wetness and body malodor.

SUMMARY OF THE INVENTION

The present invention provides simple, aqueous-based antiperspirant compositions comprising, in general, one or more antiperspirant salts, polyglycols, preferably blocked polyglycols, water, and, if desired, optional ingredients conventionally used in antiperspirant compositions. The compositions of the invention are suitable for use in a number of different cosmetic manufactured forms for application onto the body and skin surface. The compositions have excellent efficacy in combatting body malodor and perspiration and are cosmetically aesthetic. The antiperspirant compositions of the invention apply easily onto the skin surface, dry quicky, are not perceived as feeling sticky, tacky or gritty, and leave no visible residue following application.

It is an object of the invention to provide stable, aqueous-based antiperspirant compositions containing polyglycols for cosmetic use which very effectively deliver non-tacky, water-soluble antiperspirant active materials to the skin for use in combatting perspiration and body malodor, e.g., in axillary regions of the human body, by applying the antiperspirant compositions to the human body, e.g., to the skin in axillary regions of the body.

It is another object of the invention to provide cosmetic compositions of the above-described antiperspirants which do not exhibit tackiness, which feel uniform and dry after application, do not feel greasy or oily, are applied clear to the skin and remain clear and clean, i.e., have no visible cakey or chalky residue after application, regardless of the forms in which the antiperspirant compositions are delivered (e.g., roll-on or aerosol, and the like).

It is yet another object to provide an aqueous-based antiperspirant composition for use in methods for treating or preventing human malodor associated with perspiration and sweating, especially underarm malodor. The methods comprise applying to the skin of a human a safe and effective amount of the antiperspirant compositions of the invention.

Yet another object of the invention is to provide an aqueous-based antiperspirant solution technology utilizing polyglycols that minimizes or eliminates tack, is quick drying and clear. In accordance with the invention the antiperspirant solution technology is suitable for a wide variety of different delivery forms, has acceptable and advantageous organoleptic qualities, and costs significantly less than currently available antiperspirant products, e.g., clear roll-on products. The solution technology of the invention is also economical and easy to manufacture.

Further objects and advantages afforded by the invention will be apparent from the detailed description hereinbelow.

DETAILED DESCRIPTION OF THE INVENTION

The present invention provides fully soluble, aqueous-based antiperspirant compositions for reducing or inhibiting sweating and perspiration. In general, the compositions provide simple and elegant formulations which comprise one or more antiperspirant salts in combination with polyglycols, preferably blocked polyglycols, and water. All of the components of the antiperspirant compositions of the invention are soluble and are in solution in the aqueous-based compositions. The compositions of the invention deposit an effective and suitable amount of active antiperspirant material when the compositions are applied to and rubbed onto the skin, e.g., in axillary regions of the body (i.e., the compositions have good pay-off properties). Another advantage of the antiperspirant compositions of the invention is that they are simple to produce and avoid the use of multiphase systems and emulsions. Blocked polyglycols as used herein encompasse molecules that are comprised of alternating sections of one chemical composition (e.g., PPG) separated by sections of a different chemical nature (e.g., POE).

The component polyglycols of the compositions have been newly discovered as novel classes of emollient solvents that have the unique ability, when mixed with aqueous solutions of the popular antiperspirant salts, to form clear solutions which are physically and chemically stable, do not reduce the efficacy of the antiperspirant salts in the compositions, and do not feel wet upon application to the skin. Moreover, the polyglycols formulated in the antiperspirant compositions of the invention serve to reduce or eliminate the stickiness and tack of the antiperspirants and produce no visible residue in the underarm as they spread and dry upon application. In addition, these novel compositions do not sting or burn upon application, and do not increase the irritancy of the antiperspirant salts in the compositions, in contrast to ethanol. In accordance with the invention, the novel antiperspirant compositions comprising polyglycols do not need to contain significant amounts of alcohol components.

The presence of the polyglycols in the antiperspirant compositions of the invention leads to the minimization, reduction, or elimination of tack. Thus, the polyglycols, for example, PPG-2-Buteth-3, serve as detackifiers in the final compositions as described herein. In addition, such polyglycols can also function as emollients for improvement of the organoleptic qualities of the compositions of the invention. It is believed that tack can be attributed to an abundance of hydroxyl groups, mainly in the antiperspirant active and water components, but also in excipient ingredients of antiperspirant compositions. An excess of hydroxyl groups, in turn, causes subsequent hydrogen bonding on the skin. Nonlimiting examples of typical excipient ingredients in such antiperspirant formulations which are believed to be associated with the above-mentioned skin hydrogen bonding are acid-stabilized glyceryl monostearate, sodium lauryl sulfate, sodium cetyl sulfate, triethanolamine lauryl sulfate, alkyl aryl sulfates, hexitol esters of the common fatty acids and their polyoxyethylene derivatives, and polyoxyethylene ethers.

Thus, the presence of blocked polyglycols in the novel antiperspirant formulations or compositions of the invention was discovered to minimize the hydrogen bonding and consequently minimize the perception and the degree of tack on the skin. Indeed, the results of sensory studies (Example 1) showed very little tack after applying an exemplary formulation of the invention, comprising one or more blocked polyglycols, versus a high degree and perception of tack using a emulsion-based, commercially-available antiperspirant formulation (e.g., Ban Roll-on).

In general terms, the polyglycols for use in the invention are included as members of the class of polyethylene or polypropylene oxide derivatives, for example, the linear polymers of ethylene and propylene oxides having the general formula:

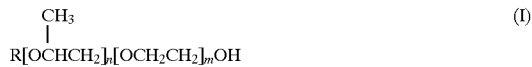

wherein m may be 0; however, m is generally greater than n; for example, n is from about 1 to 30, preferably 2 to 20; and m is from about 2 to 40, preferably 3 to 30; and R is an alkyl, for example, methyl, ethyl, propyl, isopropyl, butyl, isobutyl, pentyl, hexyl, glyceryl and the like. Liquid, water-soluble blocked polyglycols are presently preferred in the compositions of the invention.

More particularly and in a nonlimiting sense, butanol-based (i.e., buteth) polyglycols having a chain length as depicted in the following formula:

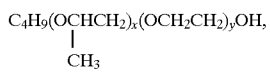

wherein, x ranges from an average value of about 2 to 33, and y ranges from an average value of about 3 to 45, and which are compatible with the active antiperspirant salts (e.g., aluminum and zirconium salts) are employed in the compositions of the invention.

Moreover, water-soluble polyglycols which are blocked polymers (blocked polyglycols) having a molecular weight of from about 200 to 20,000, preferably, about 250 to about 5000, and more preferably about 270 to 2000, are envisioned for use in the compositions of the invention.

The chemical formulae and definitions of a number and variety of blocked polyglycols suitable for use as emollient solvents in the antiperspirant compositions of the invention, and as described further hereinbelow, are found in the CTFA Cosmetic Ingredient Handbook, Monographs, Second Edition, Eds. John A. Wenninger and G. N. McEwen, Jr., Ph.D., J. D., Washington, D.C., 1992, which is known to skilled practitioners in the art, and the contents of which are herein incorporated by reference.

Examples of particular polyglycols for use in the invention include, but are not limited to, those which are commercially available as fluids and lubricants from Union Carbide under the registered trademark designation UCON®. Such UCON® compounds suitable for use in the invention, and their solubilities in various solvents at 25° C., are described in the standard product booklet/handbook "UCON® Fluids and Lubricants", which is incorporated herein by reference. It will be understood by those skilled in the art that the UCON® products also correspond to a more general designation of polyglycol chemical compounds known in the art. As a particular example of several name designations which define the same compound, the UCON® product 50-HB-55 is also known as PPG-2-Buteth-3; PPG-2-Buteth-3 is, in turn, also known in the art as polyoxyethylene (3) polyoxypropylene (2) monobutyl ether and as polyoxypropylene (2) polyoxyethylene (3) monobutyl ether, as described in the CTFA Cosmetic Ingredient Handbook.

Further nonlimiting examples of water-soluble polyglycols for use in the novel antiperspirant compositions of the invention include the UCON® polyglycols of the 50-HB series of fluids and lubricants which comprise alcohol starting polymer chemical structures containing equal amounts by weight of oxyethylene and oxypropylene groups and which have one terminal hydroxyl group. Such exemplary UCON® 50-HB compounds have a range of molecular weights and viscosities, and all are water-soluble. More particularly, a preferred polyglycol, called UCON® 50-HB-55 (also known as PPG-2-Buteth-3), has a molecular weight of 270; UCON® 50-HB-100 (also known as PPG-3-Buteth-5) has a molecular weight of 400; UCON® 50-HB-170 (also known as PPG-5-Buteth-7) has a molecular weight of 730; UCON® 50-HB-260 has a molecular weight of 1000; UCON® 50-HB-400 has a molecular weight of 1200; UCON® 50-HB-660 has a molecular weight of 1700; UCON® 50-HB-2000 has a molecular weight of 2900; UCON® 50-HB-3520 has a molecular weight of 3200; and UCON® 50-HB-5100 (also known as PPG-33-Buteth-45) has a molecular weight of 4000.

Another exemplary, but nonlimiting, class of polyglycols for use in the compositions of the invention includes the UCON® 75-H series of fluids and lubricants, which are a class of water-soluble, diol started polymers having two terminal hydroxyl groups (R=H). These polymers contain 75 weight percent oxyethylene and 25 weight percent oxypropylene groups. Specific but nonlimiting examples of the 75-H fluids useable in the compositions of the invention include: UCON® 75-H-450 having a molecular weight of 1050; 75-H-1400 having a molecular weight of 2500; 75-H-90,000 having a molecular weight of 12,000; and 75-H 1400.

Other examples of polyglycols suitable for use in the compositions of the invention include, but are not limited to, polypropylene glycol (17) or PPG-17; polypropylene glycol P-2000 or PPG-26; polypropylene glycol 4000 or PPG-30; PPG-9 (or Witconol PPG-400); PPG-34; PPG-10 butanediol; PPG-12-Buteth-16; PPG-15-Buteth-20; PPG-20-Buteth-30; PPG-24-Buteth-27; PPG-26-Buteth-26 (also known as Witconol APEB); PPG-28-Buteth-35; and PPG-2 Methyl Ether.

For convenience and clarity of understanding, Table 1 sets forth a number of exemplary blocked polyglycols for use in accordance with the invention and described by their CTFA designations, technical names, and tradenames.

TABLE 1

| CTFA Designation | Technical Name | Tradename |
|---|---|---|
| PPG-9 | polyoxypropylene (9) polypropylene glycol (9) | Witconol PPG-400 (Witco) |
| PPG-17 | polyoxypropylene (17) polypropylene glycol (17) | |
| PPG-26 | polyoxypropylene (26) polypropylene glycol (26) | Hodag PPG 2000 (Calgene) |
| PPG-30 | polyoxypropylene (30) polypropylene glycol (30) | Polyglycol P-4000 (Dow) |
| PPG-34 | polyoxypropylene (34) polypropylene glycol (34) | Witconol CD-17 (Witco) |
| PPG-10 Butanediol | | Probutyl DB-10 (Croda, Inc.) |
| PPG-2 Methyl ether | dipropylene glycol monomethyl ether | Dowanol DPM (Dow Chemical) |
| PPG-4 Butyl ether | polyoxypropylene (4) butyl ether polypropylene glycol (4) butyl ether | |
| PPG-5 Butyl ether | polyoxypropylene (5) butyl ether polypropylene glycol (5) butyl ether | UCON Lubricant LB-65 (Union Carbide) |
| PPG-9 Butyl ether | polyoxypropylene (9) butyl ether polypropylene glycol (9) butyl ether | UCON Lubricant LB-13 (Union Carbide) |
| PPG-14 Butyl ether | polyoxypropylene (14) butyl ether polypropylene glycol (14) butyl ether | Fluid AP (Amerchol) |
| PPG-15 Butyl ether | polyoxypropylene (15) butyl ether polypropylene glycol (15) butyl ether | UCON Lubricant LB-285 (Union Carbide) |
| PPG-16 Butyl ether | polyoxypropylene (16) butyl ether polypropylene glycol (16) butyl ether | Hodag PB-300 (Calgene) |
| PPG-2 Buteth-3 | polyoxyethylene (3) polyoxypropylene (2) monobutyl ether polyoxyethylene (2) polyoxypropylene (3) monobutyl ether | UCON Lubricant 50-HB-55 (Union Carbide) |
| PPG-3 Buteth-5 | polyoxyethylene (5) polyoxypropylene (3) monobutyl ether polyoxyethylene (3) polyoxypropylene (5) monobutyl ether | UCON Lubricant 50-HB-100 (Union Carbide) |
| PPG-5 Buteth-7 | polyoxyethylene (5) polyoxypropylene (7) monobutyl ether | UCON Lubricant 50-HB-170 (Union Carbide) |
| PPG-9 Buteth-12 | polyoxyethylene (9) polyoxypropylene (12) monobutyl ether polyoxyethylene (12) polyoxypropylene (9) monobutyl ether | 50-HB-400 (Amerchol) |
| PPG-12 Buteth-16 | | 50-HB-660 (Amerchol) |

TABLE 1-continued

| CTFA Designation | Technical Name | Tradename |
| --- | --- | --- |
| PPG-15 Buteth-20 | polyoxyethylene (20) poly-oxypropylene (15) mono-butyl ether polyoxyethylene (15) polyoxypropylene (20) monobutyl ether | |
| PPG-20 Buteth-30 | polyoxyethylene (20) poly-oxypropylene (30) mono-butyl ether polyoxyethylene (30) polyoxypropylene (20) monobutyl ether | 50-HB-2000 (Amerchol) |
| PPG-24 Buteth-27 | polyoxyethylene (24) poly-oxypropylene (27) mono-butyl ether polyoxyethylene (27) polyoxypropylene (24) monobutyl ether | Tergitol XD Surfactant (Union Carbide) |
| PPG-26 Buteth-26 | polyoxyethylene (26) poly-oxypropylene (26) mono-butyl ether | Witconol APE (Witco) |
| PPG-28 Buteth-35 | polyoxyethylene (28) poly-oxypropylene (35) mono-butyl ether polyoxyethylene (35) polyoxypropylene (28) monobutyl ether | UCON Fluid 50-HB-352 (Amerchol) |
| PPG-33 Buteth-45 | polyoxyethylene (33) poly-oxypropylene (45) mono-butyl ether polyoxyethylene (45) polyoxypropylene (33) monobutyl ether | UCON Fluid 50-HB-510 (Amerchol) |

Several examples of blocked polyglycols which are not water soluble, but which might be used in the compositions in suitable amounts under appropriate conditions and with appropriate amounts of the other component ingredients include PPG-4 Butyl Ether; PPG-5 Butyl Ether; PPG-9 Butyl Ether; PPG-14 Butyl Ether; PPG-15 Butyl Ether; PPG-16 Butyl Ether, and the like.

The polyglycols are present in the compositions of the invention in an amount effective to solubilize and to reduce or eliminate the perception of tackiness or stickiness of the composition. The polyglycols are present in the final antiperspirant composition in an amount of about 2% to 60% by weight, preferably about 5% to 50% by weight, more preferably, about 10% to 30%, by weight based on the total weight of the composition. More than one blocked polyglycol may be formulated into the compositions, as exemplified, such that the final antiperspirant formulations contain a mixture or combination of polyglycols of appropriate effective amount, in % by weight.

In an embodiment of the invention, liquid, water-soluble polyglycol ethers are formulated into the antiperspirant compositions. Although there are many water-soluble polymers of ethylene oxide, propylene oxide and copolymers of ethylene and propylene oxides, those particularly useful to meet the criteria for producing elegant, stable, clear antiperspirant solutions in this embodiment have one of the terminal hydroxyl groups reacted to form an ether. More specifically, such water-soluble polyglycol ethers are methyl, ethyl, butyl or glyceryl ethers of polyethylene, polypropylene or copolymers of ethylene and propylene oxides as set forth hereinbelow:

1) Polyethyleneglycol Ethers having the formula:
$R_2[OCH_2CH_2]OH$, wherein $R_2 = C_1$ to $C_6$ alkyl and glyceryl, and n=6 to 16.
Examples of polyethyleneglycol ethers for use in this embodiment, include, but are not limited to:

| CTFA Designation | Tradename |
| --- | --- |
| PEG-6 Methyl ether | Carbowax MPEG 350 (Union Carbide) |
| PEG-10 Methyl ether | Carbowax MPEG 550 (Union Carbide) |
| PEG-16 Methyl ether | Carbowax MPEG 750 (Union Carbide) |

2) Polypropyleneglycol Ethers having the formula:

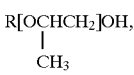

wherein $R_1 = C_1$ to $C_4$ alkyl and glyceryl, and n=2 to 10.
Examples of polypropyleneglycol ethers for use in this embodiment, include, but are not limited to:

| CTFA Designation | Tradename |
| --- | --- |
| PPG-2 Methyl ether | Dowanol DPM |
| PPG-3 Glyceryl ether | Dow Polyglycol PT 250 |
| PPG-10 Glyceryl ether | Dow Polyglycol PT 700 |

3) Polyethylene Polypropylene Glycol Ethers having the formula:

wherein $R = C_1$ to $C_6$ alkyl and glyceryl; n=1 to about 30, preferably 2 to 20; and m=about 2 to 40, preferably 3 to 30. In one aspect, of the invention the polyglycol is a $C_1$ to $C_6$ alkyl or glyceryl ether of polyoxyethylene and polyoxypropylene in which n=2 to 7 and m=3 to 10, with R preferably being butyl.
Examples of polyethylene polypropylene glycol ethers for use in this embodiment, include, but are not limited to:

| CTFA Designation | Tradename |
| --- | --- |
| PPG-2 Buteth 3 | Ucon 50 HB 55 (Union Carbide) |
| PPG-3 Buteth 5 | Ucon 50 HB 100 (Union Carbide) |
| PPG-5 Buteth 7 | Ucon 50 HB 170 (Union Carbide) |
| PPG-7 Buteth 10 | Ucon 50 HB 260 (Union Carbide) |

Examples of antiperspirant active compounds, i.e., active salts such as astringent antiperspirant metal salts, which are suitable for use in preparing the antiperspirant compositions in accordance with the invention include, but are not limited to, typical aluminum and aluminum zirconium (Al/Zr) salts that are familiar to those skilled in the art. More particular examples of antiperspirant salts include, but are not limited to, aluminum chlorohydrate, sodium aluminum chlorohydrate, aluminum sesquichlorohydrate, aluminum bromohydrate, aluminum halides (e.g., aluminum chloride), aluminum hydroxyhalides, sodium aluminum chlorohydroxylactate, buffered aluminum sulfate, aluminum chlorohydrex, aluminum hydroxide, aluminum oxychloride, aluminum oxysulfate, aluminum-zirconium compounds, such as aluminum-zirconium trichlorohydrex-gly, aluminum-zirconium tetrachlorohydrex-gly, aluminum-zirconium pentachlorohydrex-gly, aluminum-zirconium octachlorohydrex-gly, aluminum-zirconium trichlorohydrate, aluminum-zirconium pentachlorohydrate, aluminum-zirconium tetrachlorohydrate, aluminum-zirconium chloride, aluminum-zirconium sulfate, and potassium aluminum sulfate. Other suitable astringent metal salts include those of zirconium, such as zirconyl oxyhalides, zirconyl hydroxylialides (e.g., zirconyl hydroxychloride) and zirconium lactate. Mixtures, complexes and combinations of the antiperspirant metal salts are also suitable to use. Zirconium compounds as disclosed in U.S. Pat. No. 4,120,948 to Shelton; in U.S. Pat. No. 3,679,068; and in British Patent Specification No. 2,144,992 to Callaghan et al. may be used. Aluminum compounds are described in U.S. Pat. No. 3,887,692, 3,904,741, 4,359,456; and in British Patent Specification No. 2,048,229 and 1,347,950. In addition, aluminum and zirconium salts for use in the antiperspirant compositions of the invention may be found by the practitioner and are described in the CTFA Cosmetic Ingredient Handbook, Monographs (1992), for example, at pages 15–20.

Nonlimiting examples of aluminum and zirconium salts that are presently preferred in the compositions of the invention are available from the chemical company Reheis® Inc., particularly, aluminum-zirconium complexes commercially available under the registered trademark designation REACH®. The CTFA nomenclature corresponds to particular REACH® products as follows: REACH®AZP 701, 902, and 908 aluminum-zirconium complexes are aluminum-zirconium tetrachlorohydrex-gly pursuant to CTFA nomenclature; REACH®AZZ 902 aluminum-zirconium complex is aluminum-zirconium trichlorohydrex-gly pursuant to CTFA nomenclature; and REACH®AZO 902 and 908 aluminum-zirconium complexes are aluminum-zirconium octachlorohydrex-gly pursuant to CTFA nomenclature.

The particular characteristics of the REACH® series of antiperspirant actives are set out in Tables 2 and 3, as presented in Reheis®'s REACH® product brochure:

TABLE 2

REACH ® Aluminum Chlorohydrates

| Parameter | REACH® 101 & 103 | REACH ® 501 | REACH® 501 Solution |
|---|---|---|---|
| % $Al_2O_3$ | 46.0–48.5 | 46.0–48.0 | 20.0–22.0* |
| % Cl | 15.8–17.5 | 15.8–16.8 | 7.2–7.7 |
| Al:Cl Atomic Ratio | 1.9:1.0–2.1:1.0 | 19:1.0–2.1:1.0 | 1.9:1.0–2.1:1.0 |
| Fe (ppm) | NMT 125 | NMT 100 | NMT 50 |
| pH (15% w/w solution) | 4.0–4.4 | 4.0–4.4 | N/A |
| pH (30% w/w solution) | N/A | N/A | 4.0–4.5 |
| Particle size | | | |
| % thru 105 microns | NLT 9.98% | NLT 99.8% | N/A |
| % thru 44 microns | NLT 97.0% | NLT 97.0% | N/A |
| Appearance | White to off-white powder | White to off-white powder | Clear to slightly turbid solution |
| CTFA Nomenclature | Aluminum Chlorohydrate | Aluminum Chlorohydrate | Aluminum Chlorohydrate |

TABLE 3

REACH ® Aluminum-Zirconium Complexes

| Parameter | REACH® AZP 701, 902 & 908 | REACH ® AZZ 902 | REACH® AZO 902 & 908 |
|---|---|---|---|
| % Al | 14.5–15.5 | 14.0–15.2 | 16.0–17.5 |
| % Zr | 13.0–15.5 | 13.6–16.3 | 5.5–6.5 |

TABLE 3-continued

REACH ® Aluminum-Zirconium Complexes

| Parameter | REACH® AZP 701, 902 & 908 | REACH ® AZZ 902 | REACH® AZO 902 & 908 |
|---|---|---|---|
| % Cl | 17.0–18.5 | 13.3–17.5 | 22.5–25.5 |
| % Glycine | 10.5–13.5 | 13.5–16.5 | 10.0–15.0 |
| Metals: Chloride Ratio | 0.9:1.0–1.5:1.0 | 1.5:1.0–2.1:1.0 | 0.9:1.0–1.2:1.0 |
| Al:Zr Atomic Ratio | 3.4:1.0–3.8:1.0 | 3.2:1.0–3.6:1.0 | 8.5:1.0–10.0:1.0 |
| Fe (ppm) | NMT 100 | NMT 100 | NMT 100 |
| pH (15% w/w Solution) | 3.7–4.1 | 3.7–4.5 | 3.2–4.0 |
| Particle size | | | |
| % thru 37 microns | NLT 100.0% | NLT 100.0% | NLT 100.0% |
| % thru 10 microns | NLT 95.0% | NLT 95.0% | NLT 95.0% |
| Appearance | White to off-white powder | White to off-white powder | White to off-white powder |
| CTFA Nomenclature | Aluminum-Zirconium Tetrachlorohydrex GLY | Aluminum-Zirconium Trichlorohydrex GLY | Aluminum-Zirconium Octachlorohydrex GLY |

Another particular but nonlimiting example of an aqueous aluminum zirconium salt that is quite suitable for employment in the compositions of the invention is 35% aqueous aluminum zirconium tetrachlorohydrex-Gly, commercially available as Westchlor® ZR 35B from Westwood Chemical Corporation, Middletown, N.Y. Westchlor® ZR 35B is a conventional tetra salt with an Al/Zr atomic ratio of 3.5:1 and a metal/chloride ratio of 1.4:1, and is also known to those in the art as AZG or ZAG.

The Food and Drug Administration's OTC Panel On Antiperspirants has adopted certain nomenclature and specifications for various aluminum zirconium polychlorohydrates that are useful in the present invention. These are set out in Table 4 below:

TABLE 4

| Panel Adopted Nomenclature | Metal-Halide Ratio Range | Al/Zr Ratio Range |
|---|---|---|
| Aluminum zirconium trichlorohydrate | 2.1 down to but not including 1.5:1 | 2.0 up to but not including 6.0:1 |
| Aluminum zirconium tetrachlorohydrate | 1.5 down to and including 0.9:1 | 2.0 up to but not including 6.0:1 |
| Aluminum zirconium pentachlorohydrate | 2.1 down to but not including 1.5:1 | 6.0 up to and including 10.0:1 |
| Aluminum zirconium octachlorohydrate | 1.5 down to and including 0.9:1 | 6.0 up to and including 10.0:1 |

It will be appreciated by those skilled in the art that glycine may be bound in the aluminum-zirconium complexes of the antiperspirant active metal salt. In the compositions of the invention, aluminum-zirconium complexes containing glycine are presently preferred.

Another nonlimiting example of an aluminum metal salt particularly suitable for employing in the compositions of the invention is aluminum chlorohydrate, which may be represented by the formula:

$$[Al_2(OH)_m]Cl_n,$$

where m+n=6, and which encompasses a range of aluminum to chloride ratios from 2.1 down to but not including 1.9 to 1. Also preferred are aluminum chlorohydrates commercially available under the registered trademark designation REACH®, as described in Table 2.

It will be appreciated by those skilled in the art that products similar to the aforementioned antiperspirant metal salts are also manufactured by Dow Corning Company. Preferably, in the compositions comprising aluminum chlorohydrate antiperspirant salt, an aqueous solution of the antiperspirant (e.g., a solution at a concentration of about 50% to 60% in water) can be used. The 50% ACH solution in water can be purchased directly as such from the supplier.

The active antiperspirant ingredients are solubilized in the compositions of the invention in an effective antiperspirant amount to reduce or eliminate perspiration, wetness and body malodor, i.e., in a sufficient amount to have an effect to reduce body malodor by reducing wetness and the flow of perspiration where applied. By reduction of body malodor is meant generally that there is less body malodor or wetness from perspiration after application of the composition to a person's skin compared with no application onto the skin. Such reduction can be due to a masking of the malodor, reduction of the levels of bacteria which produce the malodorous materials, e.g., from perspiration or sweat, reduction of perspiration, and the like. It is generally appreciated that antiperspirant materials primarily act to reduce body malodor by reducing the production of perspiration or sweat.

In general, the active antiperspirant (e.g., antiperspirant metal salt) is present in the compositions in amounts that are the same as those normally used in antiperspirant compositions. Typically, the amount is on an active basis and can be from about 2% to about 60% by weight of the composition, preferably about 5% to about 35%, and more preferably up to about 26%. On an anhydrous basis, the amount of antiperspirant is commonly about 5% to about 26%. More particularly, the maximum use level for ACH is typically up to about 26% by weight, while the maximum use level for AZG is typically up to about 20% by weight, on an anhydrous basis. For deodorant compositions, the amount of antiperspirant may be less than 8%.

The compositions formulated in accordance with the invention can include optional ingredients, in addition to the above-detailed ingredients, i.e., antiperspirant metal salts, blocked polyglycols, and water, to further enhance clarity, structural integrity, antiperspirant performance, cosmetic appeal, or to facilitate manufacturing. The aqueous-based antiperspirant compositions of the present invention contain sufficient water to form a solution containing the essential and optional ingredients, suitably from about 20% to about 61% by weight of the total composition.

Nonlimiting, exemplary classes of cosmetic ingredients or other additives may optionally be used in the aqueous antiperspirant composition solutions of the invention in amounts of about 0.1% to 40%, preferably about 0.5% to 20%, more preferably, about 1% to 10% by weight. Such optional ingredients include, but are not limited to, emollients; emulsifiers; humectants; detergent and emulsifier intermediates; suspending and dispersing agents; antioxidants; preservatives; antimicrobial compounds; buffers; chelating agents; coupling agents; cosolvents, solvents, and solubilizers; clarifiers and detackifiers; foaming boosters; suspending and dispersing agents; thickening agents; penetrants; gelling agents; hardeners; strengtheners; opacifiers; waxes; dyes; colorants; fragrances; and mixtures or combinations thereof, and other components typically used in antiperspirant formulations. If necessary or desired, the antiperspirant may also include, illustratively, deodorant materials, including, but not limited to, antimicrobial compounds, antioxidants, and deodorant fragrances.

In general, the presently preferred optional additive ingredients for the compositions of the invention include, but are not limited to, emollients; suspending and dispersing agents; buffers; chelating agents; coupling agents; cosolvents, solvents and solubilizers; clarifiers and detackifiers; fragrances; perfumes; and combinations or mixtures thereof. More preferred optional ingredients include suitable amounts of solvents, cosolvents and solubilizers for optimum product clarity, e.g., dipropylene glycol or polyethylene glycol or surfactants, e.g., Brij 78, in amounts of about 0.1% to 40% by weight; perfumes and colors, in amounts of about 0.1% to 2% by weight; and antimicrobial compounds in amounts of about 0.01% to 2% by weight.

In addition, the pH of the compositions of the invention is about 2.5 to 6.5, preferably, about 3.0 to 5.5, more preferably about 3.5 to 4.5. A low pH can be attributed to the antiperspirant active metal salts used in the compositions, which are acidic in nature. In general, the components and additives formulated into the compositions of the invention are acid-stable and acid-compatible for optimum stability and shelf-life.

Several of the above-listed optional ingredients that may be used in the compositions of the invention are considered more particularly hereinbelow:

Solvents, Cosolvents, and Solubilizers:

If desired, relatively small amounts of solvents and cosolvents, other than water, may be formulated into the compositions of the invention to assist in the solubilization of component ingredients of the compositions and for optimum product clarity. Commonly employed solvents and cosolvents are selected from dihydroxy aliphatic alcohols containing from 3 to 5 carbon atoms, and include, for example, dipropylene glycol, 1,3-propylene glycol; 1,2-propylene glycol, 1,3-butylene glycol; 1,4-butylene glycol; and 1,5-dihydroxy pentane.

By far the most preferred cosolvent in the compositions of the invention is dipropylene glycol. However, dihydroxy aliphatic ethers, containing from 6 to 10 carbon atoms, such as dibutylene glycol, may be also utilized. Cosolvents are typically employed at concentrations of from about 0% to about 40%, preferably about 10% to 25%, more preferably about 5% to 15%.

An additional exemplary class of compounds having solubilizer function in the antiperspirant compositions of the present invention is that of the alkyoxylated alcohols, such as ceteareth-15, ceteareth-16, ceteareth-17, ceteareth-18, ceteareth-20, ceteareth-23, ceteareth-25, ceteareth-27, ceteareth-28, and ceteareth-30, with ceteareth-20 being especially suitable for solubilizer function in the compositions of the invention. As known to those in the art, the ceteareths are further described in the CTFA Cosmetic Handbook, 1992.

Table 5 lists the CTFA designations, technical names, and tradenames of a number of exemplary cosolvents and solubilizers suitable for use in the invention:

TABLE 5

| CTFA Designation | Technical name | Tradename |
| --- | --- | --- |
| Dipropylene glycol | Di-1,2-propylene glycol | Dipropylene glycol (BASF) |
| Propylene glycol | 1,2-propanediol | 1,2-propylene glycol USP (BASF) |
| Butylene glycol | 1,3-butanediol 1,3-butylene glycol | |
| Ceteareth-15 | PEG-15 cetyl stearyl ether | Tego-Care 215 (Goldschmidt) |
| Ceteareth-16 | PEG-16 cetyl stearyl ether | Simulsol 5719 (Seppic) |

TABLE 5-continued

| CTFA Designation | Technical name | Tradename |
|---|---|---|
| Ceteareth-17 | PEG-17 cetyl stearyl ether | Procol CS-17 (Protameen) |
| Ceteareth-18 | PEG-18 cetyl stearyl ether | Marlowet TH18 (Huls America) |
| Ceteareth-20 | PEG-20 cetyl stearyl ether | Eumulgin B-2 (Henkel) |
| Ceteareth-23 | PEG-23 cetyl stearyl ether | Atlas G-3713 (ICI Surfactant) |
| Ceteareth-25 | PEG-25 cetyl stearyl ether | Cresnophor A-25 (BASF) |
| Ceteareth-27 | PEG-27 cetyl stearyl ether | Plurafac A-38 (BASF) |
| Ceteareth-28 | PEG-28 cetyl stearyl ether | Marlowet Fox (Huls America) |
| Ceteareth-30 | PEG-30 cetyl stearyl ether | Lipocol SC-30 (Lipo) |

Clarifiers and Detackifiers:

The compositions of the invention may contain small amounts of one, or several, emollients, surfactants and other water soluble or insoluble components which may additionally function to increase clarity or as antitacking agents to prevent stickiness of the compositions after they have dried on the skin surface. Emollients enhance the feel of the compositions and the ease with which they can be applied. Emollients include lubricants and other materials used to enhance the organoleptics of an antiperspirant product, as is well known in the art. Indeed, in the compositions of the invention the blocked polyglycols serve as effective emollient solvents, thereby obviating other emollient additives, unless desired or necessary, as optional additives in the compositions.

In addition, the compositions may optionally contain semipolar products which are soluble or compatible with propylene glycol or dipropylene glycol, which are known to those skilled in the art and which can be utilized in the practice of the invention. Clear, liquid semipolar emollients and surfactants may be used to attain improved clarity under all temperature conditions, if desired.

One exemplary class of compounds meeting the above description is disclosed in U.S. Pat. No. 4,759,924. Certain of these compounds are commercially available under the trade name PPG-5-Ceteth 20 (available as Procetyl AWS), PPG-3-Myreth-3, PEG-20-Laurate and Poloxamer 335.

The following Table 6 lists other semipolar materials which may be employed. They are identified by their trade names, the CTFA Cosmetic Handbook designation, and the commercial source of the material.

TABLE 6

| Trade Name | CTFA Designation | Source |
|---|---|---|
| 1. Arosurf 66-E2 | Isosteareth-2 | Sherex |
| 2. Arlasolve 200 | Isoceteth-20 | ICI |
| 3. Dermol G-76 | Glycereth-7-Benzoate | Alzo |
| 4. Brij 30 | Laureth-4 | ICI |
| 5. Arosurf 66PE12 | PPG-3 Isosteareth-9 | Sherex |
| 6. Cetiol HE | PEG-7-Glycerol Cocoate | Henkel |
| 7. Aethoxal B | PPG-5-Laureth-5 | Henkel |
| 8. Emulgin L | PPG-2-Ceteareth-9 | Henkel |
| 9. Sandoxylate SX-408 | PPG-2-Isoceteth-4 | Sandoz |
| 10. Sandoxylate SX-424 | PPG-2-Isoceteth-12 | Sandoz |
| 11. Procetyl AWS | PPG-5-Ceteth-20 PPG-3-Myreth-3 | Croda |

Other useful materials having the desired properties which can be optionally employed in the compositions of the invention include diisopropyl seacate, myristyl lactate and isopropyl myristate.

Clarifiers and detackifiers may be employed typically at a concentration level of from about 0.5% to 12%, preferably, about 1% to 10%, more preferably about 1.5% to 8%.

Perfumes and fragrances:

Perfumes and fragrances normally employed in cosmetic compositions such as the antiperspirant compositions of this invention may be employed herein if desired. If employed, the perfumes or fragrances are acid-stable stable and are typically present in the compositions at a concentration of 0.01% to about 2%, preferably from about 0.05% to 2%.

Antimicrobial compounds:

Antimicrobial compounds (e.g., antibacterial compounds) which may be optionally formulated into the compositions of the invention, if desired, will be the same as those which are normally employed in compositions of this nature. Antibacterial compounds include, for example, Triclosan, benzalkonium chloride, benzethonium chloride, and zinc phenolsulfonate. Typically, the compositions may contain about 0.01% to about 2% antibacterial agent, preferably about 0.05% to 1.5%.

The compositions may additionally contain coloring agents, botanicals, or other components used in such compositions, provided that such additives are acid-stable, and are soluble in and compatible with (or can be formulated as such) the other components in the compositions. An important factor in the final stability, clarity, and organoleptics of the antiperspirant products of the invention is the compatibility and solubility of the various component ingredients of the novel compositions as described. In accordance with the invention, the components of the final compositions are completely in solution, thereby creating the novel and versatile aqueous solution technology of the invention.

It will be appreciated by those having skill in the art that the aqueous-based antiperspirant compositions of the invention are effective and useful as common, aqueous-based solution formulations which may, in turn, be formulated into a variety of cosmetic dosage and/or delivery forms for application and administration of antiperspirant active materials. Thus, in accordance with the invention, the aqueous-based antiperspirants may be manufactured/produced in the following forms, which are not intended to be limiting: creams; gels; solids (e.g., barrier pack; liquistik); sprays (e.g., pump sprays); aerosols (e.g., true clear aerosol); roll-ons (e.g., for quicker drying roll-ons); opacified roll-ons; foams and the like. Although not a requirement for use, the preferred modes of applying the antiperspirant compositions of the invention are as roll-ons, sprays, or aerosols. The final antiperspirant products comprising the compositions of the invention are preferably clear upon application and drying, i.e., transparent to the transmission of light, such that minimal white residue or film is visible on the skin at the application site. If the antiperspirant solutions of the invention were to be formulated in a solid or gelled form, they would preferably allow sufficient light to pass through to enable an observer to see without difficulty an image, e.g., lettering, that is placed directly behind and in contact with the solid or gel form.

In general, the process by which the aqueous-based antiperspirant compositions are formulated is as follows:
1. The antiperspirant metal salt solution is mixed with water;
2. The other liquid components are added while mixing at room temperature; and
3. The solid solubilizer is melted with the perfume at 50° C. and added to the mixture while stirring.

The process of preparing the compositions is efficient, easy, and is most suitable for the present aqueous formulations of the invention. More particularly and with regard to the formulation of the component ingredients as exemplified herein, the process essentially involves heating the solubilizer, e.g., ceteareth-20, as in Examples 9 and 10, at approximately 50° C. until melted. Thereafter, the other components of the composition are mixed at room temperature in the following order: first, antiperspirant metal salt, e.g., ACH; next, deionized water; next, blocked polyglycol detackifier and emollient, e.g., PPG-2-Buteth-3; next, solvent, e.g., dipropylene glycol; and then, blocked polyglycol emollient, e.g., PPG-9 (Witconol PPG-400). While these ingredients are mixing, the melted solubilizer (ceteareth) is added and mixing is continued at room temperature until the ceteareth is completely dissolved (i.e., for about 30 minutes). It will be appreciated by those in the art that the PPG-9 blocked polyglycol can be added prior to the addition of the PPG-2-Buteth-3 blocked polyglycol, with no adverse effects and with the same resulting composition. The process of formulating the compositions is virtually the same for all of the antiperspirant compositions in accordance with the invention.

The antiperspirant compositions of this invention, when tested for effectiveness substantially as described in Federal Register, Vol. 47, Number 162, Aug. 20, 1982, are as active as commercially available compositions and are optically-clear (i.e., transparent), quick-drying and non-tacky on the user.

EXAMPLES

The examples as set forth herein are given by way of illustration only and are not to be considered limitations of this invention, many apparent variations of which may be made without departing from the spirit or scope thereof.

Example 1

A typical sensory study to evaluate each of the antiperspirant compositions prepared as described in the Examples hereinbelow is generally carried out as described in this Example.

More particularly, blind antiperspirant evaluations are completed by a total of eight panelists over the course of several testing sessions, depending upon the number of composition samples being tested. In the case of four pairs of compositions, four testing sessions are used. For example, for samples A–H, the pairs tested are A/B; C/D; E/F; and G/H. All samples are presented in pairs, but not all of the panelists receive the same pair in a given session; some panelists test pair A/B, while others test C/D, E/F, or G/H. In addition, the order of presentation of the samples within each pair is randomized to minimize position bias (e.g., A/B, B/A).

The sample antiperspirant products are applied according to the following protocol: The designated panel leader uses an automatic pipette to dispense 0.4 mL of product. To each of four sites along a 6"×2" scribed area on the volar forearm, 0.1 mL of product is dispensed. One sample is dispensed to the left arm and the second sample is dispensed to the right arm. Each panelist then applies the product using the index finger (protected by a finger cot) in four upward strokes which distributes the product over the evaluation area.

Evaluations are performed immediately after application and at 5, 10 and 20 minute intervals thereafter. All ratings are carried out on a 100 point intensity scale from 0="not at all" to 100="very much". Higher ratings indicate the presence of more of the particular characteristic being evaluated. The organoleptics and aesthetic character of the product as defined by residual skinfeel and appearance are evaluated.

Specifically, sample characteristics evaluated included, for example, gloss, stickiness or tackiness, (fold), stickiness or tackiness (tactile), particulate, oil, grease, wax, visible white residue, total residue (tactile), taut, rub-off whitening, opacity, and slipperiness. With particular regard to the evaluation of tackiness, a sample product is routinely assessed for tackiness as the product is drying on the skin after application, for example, as a roll-on. The evaluator determines the sensation of tack or stickiness of the product of the finger and the sensation of tack on the skin as the product is drying after application, for example within up to a minute, preferably within 5 to 30 seconds after application. In general for the compositions of the invention, the faster that the composition dries on the skin after application, the less tackiness is discerned or perceived by the evaluator in the sensory testing.

The results of a sensory test comparison between a current, commercial emulsion product, e.g., Ban Roll-on, and the antiperspirant composition of the invention presented in Table 7, used as a test sample and applied as a roll-on, is set forth in Table 8. In Table 7, the numbers in parentheses after each of the characteristics listed at the left side of the Table indicate the minutes after a sample was applied.

TABLE 7

|  | p-value | Commercial Roll-On (Emulsion) | Antiperspirant Composition Roll-on of the Invention |
| --- | --- | --- | --- |
| Gloss (5) | 0.0001 | 73.1 | 6.3 |
| Total Residue (visual) (5) | 0.0005 | 39.4 | 18.4 |
| Stickiness (fold) (5) | 0.0003 | 14.9 | 0.4 |
| Wet (5) | 0.01 | 13.0 | 0.0 |
| Stickiness (tactile) (5) | 0.0001 | 17.4 | 1.9 |
| Total Residue (tactile) (5) | 0.04 | 26.9 | 18.1 |
| Particulate (5) | 0.001 | 0.7 | 15.0 |
| Grease (5) | 0.02 | 18.1 | 1.9 |
| Gloss (10) | 0.04 | 29.0 | 1.4 |
| Stickiness (fold) (10) | 0.04 | 8.8 | 0.0 |
| Taut (10) | 0.04 | 25.6 | 22.5 |
| Occlusion (20) | 0.005 | 15.1 | 10.6 |
| White Residue (visual) (20) | 0.004 | 23.8 | 6.4 |
| Opacity (20) | 0.02 | 18.4 | 7.3 |
| Rub off Whitening (20) | 0.05 | 68.8 | 37.5 |

The antiperspirant formulation of the invention with which the commercial roll-on was compared in the sensory test as described in this Example is presented in Table 8:

TABLE 8

| Ingredients | Function | % wt. |
| --- | --- | --- |
| Aluminum chlorohydrate, 50% (Summit) | Antiperspirant | 44.00 |
| PPG-9 (Witconol PPG-400) | Emollient solvent | 2.00 |
| PPG-2-Buteth-3 | Emollient solvent | 10.00 |
| Dipropylene glycol | Co-solvent/solubilizer | 5.00 |
| Water, deionized (DI) | Solvent | 39.00 |
|  |  | 100.00 |

The results of this comparative sensory testing analysis showed that the commercial roll-on product displayed significantly higher scores than did the test sample of the invention for all of the significant characteristics, with the exception of particulate at 5 minutes. The commercial roll-on was found to be more glossy, sticky, wet and greasy than the test sample of the invention. The commercial product was determined to leave the skin feeling more occluded and taut and had more visual and tactile residue, which was whiter and more opaque, than the minimal or neglible residue of the test sample. Further, the commercial roll-on product produced significantly more rub-off whitening when evaluated at the end of the evaluation period. Accordingly, the antiperspirant compositions of the invention provide more pleasing organoleptics, more advantageous cosmetic characteristics and more satisfying personal aesthetics than the commercially available roll-on.

Example 2

The components presented in this Example were mixed as described to prepare an antiperspirant composition of the invention.

If the appearance of the composition was clear after formulation, the composition, as a roll-on, was briefly and initially evaluated for its organoleptic properties in the laboratory directly after its preparation. Such a first quick assessment (i.e., an initial organoleptic evaluation) was carried out by rolling the product onto the skin with three strokes from the roll-on bottle. After about 10 seconds, two fingers were used to feel the area on which the composition had been applied for degree of tack (stickiness), quickness of drying, appearance of white residue, and feel of film.

| Ingredients | % wt. |
| --- | --- |
| Aluminum chlorohydrate, 50% (Reheis) | 40.18 |
| Dipropylene glycol | 13.70 |
| PPG-14 Butyl Ether (UCON ® Fluid AP) | 9.13 |
| PPG-9 (Witconol PPG-400) | 6.85 |
| Polyglyceryl-4 oleate (Witconol-14) | 6.85 |
| Ethyl alcohol | 4.61 |
| Sodium xylene sulfonate | 8.68 |
| | 100.0% |

The appearance of the composition was clear, and the initial organoleptic evaluation determined that the final composition produced negligible tack.

Example 3

An antiperspirant composition of the invention was prepared by mixing the ingredients as presented in this Example.

| Ingredients | % wt. |
| --- | --- |
| Aluminum chlorohydrate, (Summit 303) | 44.00 |
| Dipropylene glycol | 13.70 |
| PPG-14 Butyl ether (UCON ® Fluid AP) | 9.13 |
| PPG-9 (Witconol PPG-400) | 6.85 |
| Polyglyceryl-4 oleate (Witconol-14) | 2.00 |
| Ethyl alcohol | 15.64 |
| Sodium xylene sulfonate | 8.68 |
| | 100.0% |

The appearance of the composition was clear, and the initial organoleptic evaluation determined that the final composition produced negligible tack.

Example 4

Another composition of the invention was prepared from the components as described in this Example, employing the procedure used for the above-described Examples.

| Ingredients | % wt. |
| --- | --- |
| Aluminum chlorohydrate, 50% (Summit) | 44.00 |
| Dipropylene glycol | 15.00 |
| UCON ® Fluid 5100 | 10.00 |
| Methoxy PEG 550 (Carbowax Sentry Grade 550NF, Union Carbide) | 15.00 |
| Water, deionized (DI) | 16.00 |
| | 100.00 |

The appearance of the composition was clear, and the initial organoleptic evaluation determined that the final composition was non-tacky and quick drying.

Example 5

The components presented in this Example were mixed as previously described hereinabove to prepare an antiperspirant composition having the advantageous characteristics afforded by the invention.

| Ingredients | % wt. |
| --- | --- |
| Aluminum chlorohydrate, 50% (Reheis) | 44.00 |
| PPG-2 Methyl Ether (Dowanol DPM) | 15.00 |
| Dipropylene glycol | 10.00 |
| Methoxy PEG-550 | 15.00 |
| Brij 78 | 1.00 |
| Water, deionized (DI) | 15.00 |
| | 100.00 |

The appearance of the composition was clear, and the initial organoleptic evaluation determined that the final composition was non-tacky and produced negligible residue on skin.

Example 6

Another composition of the invention was prepared by mixing the following ingredients as described.

| Ingredients | % wt. |
| --- | --- |
| Aluminum chlorohydrate, 50% (Reheis) | 44.00 |
| PPG-9-Buteth-12 | 10.00 |
| PPG-9 (Witconol PPG-400) | 2.00 |
| Dipropylene glycol | 5.00 |
| Water, deionized (DI) | 39.00 |
| | 100.00 |

The appearance of the composition was clear, and the initial organoleptic evaluation determined that the final composition was negligibly tacky and produced negligible residue.

Example 7

Another composition of the invention was prepared from the component ingredients listed below as described herein.

| Ingredients | % wt. |
| --- | --- |
| Aluminum chlorohydrate, 50% (Reheis) | 44.00 |
| PPG-2 Methyl Ether (Dowanol DPM) | 20.00 |

-continued

| Ingredients | % wt. |
|---|---|
| PPG-9 (Witconol PPG-400) | 1.00 |
| Methoxy PEG 550 | 20.00 |
| Water, deionized (DI) | 15.00 |
| | 100.00 |

The appearance of the composition was clear, and the initial organoleptic evaluation determined that the final composition was non-tacky and fast drying.

Example 8

A composition was prepared in accordance with the invention from the component ingredients as presented in this Example.

| Ingredients | % wt. |
|---|---|
| Aluminum chlorohydrate, 50% (Reheis) | 44.00 |
| PPG-2-Buteth-3 (UCON ® 50-HB-55) | 10.00 |
| PPG-9 (Witconol PPG-400) | 2.00 |
| Dipropylene glycol | 5.00 |
| Water, deionized (DI) | 39.00 |
| | 100.00 |

The appearance of the composition was clear, and the initial organoleptic evaluation determined that the final composition was non-tacky and fast drying.

Example 9

Another antiperspirant composition was prepared in accordance with the invention from the component ingredients as presented in this Example.

| Ingredients | % wt. |
|---|---|
| Aluminum chlorohydrate, 50% (Reheis) | 44.00 |
| PPG-2-Buteth-3 (UCON ® 50-HB-55) | 10.00 |
| Ceteareth-20 | 8.00 |
| PPG-9 (Witconol PPG-400) | 10.00 |
| Water, deionized (DI) | 28.00 |
| | 100.00 |

The appearance of the composition was clear, and the initial organoleptic evaluation determined that the final composition was only minimally tacky and produced no white residue.

Example 10

An antiperspirant composition was prepared in accordance with the invention from the component ingredients as presented in this Example.

| Ingredients | % wt. |
|---|---|
| Aluminum chlorohydrate, 50% (Reheis) | 44.00 |
| PPG-2-Buteth-3 (UCON ® 50-HB-55) | 13.11 |
| PPG-9 (Witconol PPG-400) | 5.11 |
| Dipropylene glycol | 8.11 |
| Ceteareth-20 | 1.00 |

-continued

| Ingredients | % wt. |
|---|---|
| Water, deionized (DI) | 27.97 |
| Fragrance | 0.70 |
| | 100.00 |

The appearance of the composition was clear, and the initial organoleptic evaluation determined that the final composition had negligible tack and successfully solubilized fragrance.

Example 11

A composition of the invention was prepared from the components listed below using the procedure described below.

| Ingredients | % wt. |
|---|---|
| Aluminum chlorohydrate, 50% (Reheis) | 44.00 |
| PPG-2 Methyl Ether (Dowanol DPM, Dow) | 15.00 |
| PPG-2-Buteth-3 | 10.00 |
| Methoxy PEG-550 | 15.00 |
| Brij 78, ICI (Polyoxyethylene 20 stearylether) | 1.00 |
| Water, deionized (DI) | 15.00 |
| | 100.00 |

The appearance of the final composition was clear and had negligible tack.

The composition of this example was prepared as follows: deionized water and aluminum chlorohydrate, 50%, were mixed. Next, PPG-2 Methyl Ether, Methoxy PEG 550, and PPG-2-Buteth-3 were added in sequence. All of these components were mixed until a clear solution was obtained. Ingredient number 5, Brij 78, was heated to 50° C. to melt. The melted Brij 78 was then added with mixing to the batch mixture of the other ingredients.

The contents of all patents, patent applications, published articles, books, references, manuals, and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A soluble, clear, aqueous-based antiperspirant composition for application onto human skin, comprising an aqueous solution of an antiperspirant metal salt present in an amount effective to reduce perspiration, the salt being selected from the group consisting of aluminum, zirconium and aluminum-zirconium (Al/Zr) salts, and at least one liquid water-soluble polyglycol that is a linear polymer of ethylene oxide and/or propylene oxide, the polyglycol having a molecular weight of from about 200 to about 20,000 and being present in the final composition in an amount effective to reduce or eliminate tackiness.

2. The composition according to claim 1 wherein said polyglycol is selected from the group consisting of:

wherein n is from about 1 to 30; m is from about 2 to 40; and R is an alkyl of from 1 to 6 carbon atoms and glyceryl;

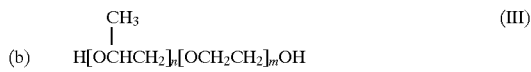

the values of m and n being selected to provide a polyglycol (III) having a molecular weight of from about 200 to about 12,000;

wherein n is from 9 to 34 when $R_1$ is H, and wherein n=1 to 30 when $R_1$ is an alkyl of from 1 to 6 carbon atoms and glyceryl;

wherein $R_2$ is $C_1$ to $C_4$ alkyl and glyceryl and m is from 6 to 16; and (e) PPG-10 butanediol.

3. The composition according to claim 1 wherein said polyglycol has the formula:

wherein x ranges from an average value of about 2 to 33, and y ranges from an average value of about 3 to 45.

4. The composition according to claim 2 wherein the polyglycol is the polyglycol of formula (I) and has a molecular weight of from about 250 to about 5000.

5. The composition according to claim 3 wherein the polyglycol is the polyglycol of formula (II) and has a molecular weight of from about 250 to about 5000.

6. The composition according to claim 5 wherein x is from 2 to 7 and y is from 3 to 10.

7. The composition according to claim 4 or 6 wherein the molecular weight of said polyglycol is from about 270 to about 2000.

8. The composition according to claim 2 wherein the polyglycol is the polyglycol of formula (III) and has a molecular weight of from about 250 to about 5000.

9. The composition according to claim 2 wherein the polyglycol is the polyglycol of formula (IV).

10. The composition according to claim 2 wherein the polyglycol is the polyglycol of formula (V).

11. The composition according to claim 2, 3, 8, 9 or 10 wherein
(a) water in the aqueous solution is present in an amount of from about 20 to about 61%;
(b) the antiperspirant salt is present in an amount of from 5 to 26%, and
(c) wherein the polyglycol is present in an amount of from about 5 to 50%, all percents being by weight of the total antiperspirant composition.

12. An aqueous based antiperspirant composition comprising by weight, based on the total weight of the composition:

A) from about 2% to about 35% antiperspirant of a water soluble antiperspirant metal salt selected from the group consisting of aluminum, zirconium and aluminum-zirconium (Al/Zr) salts, B) from about 5% to about 50% of at least one water soluble, polyglycol that is a linear polymer of ethylene oxide and/or propylene oxide selected from the group consisting of:

wherein n is from about 2 to 20; m is from about 3 to 30; and R is an alkyl of from 1 to 6 carbon atoms and glyceryl, said polyglycol having a molecular weight of from about 200 to about 5000;

the values of m and n being selected to provide a polyglycol (III) having a molecular weight of from about 200 to about 5,000;

wherein n is 9 to 34 when $R_1$ is H, and wherein n=1 to 30 when $R_1$ is an alkyl of from 1 to 6 carbons and glyceryl;

wherein $R_2$ is a $C_1$ to $C_4$ alkyl and glyceryl and m is from 6 to 16; and
(e) PPG-10 butanediol;

C) water present in an amount of from about 20% to about 61%, and

D) from about 0% to 40% of at least one cosolvent or solubilizer, said composition being a clear solution.

13. The composition according to claim 12 wherein said polyglycol has the formula (I) and wherein R is a $C_1$ to $C_4$ alkyl and glyceryl, n is from about 2 to 20 and m is from about 3 to 30.

14. The composition according to claim 13 wherein n is from 2 to 7 and m is from 3 to 10.

15. The composition according to claim 12 in which the polyglycol has the formula (IV) and wherein $R_1$ is methyl or glyceryl and n=2 to 10.

16. The composition according to claim 12 in which the polyglycol has the formula (V) and wherein $R_2$ is methyl.

17. The composition according to claim 12 wherein said polyglycol is selected from the group consisting of PPG-9; PPG-2 Methyl ether; PPG-14 Butyl ether; PPG-10 Methyl ether; PPG-2 Buteth-3; PPG-3 Buteth-5; PPG-5 Buteth-7; PPG-9 Buteth-12; PPG-12 Buteth-16; PPG-15 Buteth-20; and mixtures or combinations thereof.

18. The composition according to claim 15 wherein said polyglycol is a mixture of polyglycols selected from mixtures of PPG-2-Buteth-3 and PPG-9; PPG-2 Methyl ether and PPG-9; and PPG-9 Buteth-12 and PPG-9.

19. The composition according to claims 12 wherein said polyglycol is selected from the group consisting of PPG-3-Glyceryl-Ether; PPG-10-Glyceryl Ether, PPG-2-Buteth-3, PPG-3-Buteth-5; PPG-5-Buteth-7, PPG-7-Buteth-10; PPG-9 Buteth 12, and mixtures or combinations thereof.

20. The composition according to claim 17 wherein said polyglycol is PPG-9-Buteth-12.

21. The composition according to claim 17 wherein said polyglycol is PPG-2-Buteth-3.

22. The composition according to claim 12, 13, 14, 17 or 19 wherein said polyglycol is present in an amount of about 10% to 30% by weight, based on the total weight of the composition.

23. The composition according to claim 12 wherein said cosolvent or solubilizer is a dihydroxy aliphatic alcohol containing from 3 to 5 carbon atoms or a dihydroxy aliphatic ether containing from 6 to 10 carbon atoms, the cosolvent or solubilizer being present in an amount of from 5 to 25%.

24. The composition according to claim 23 wherein said cosolvent or solubilizer is propylene glycol or dipropylene glycol.

25. The composition according to claim 13 in which the polyglycol has the formula (III).

26. A method of reducing or inhibiting perspiration and body malodor or an individual, comprising the step of applying the composition according to claim 12 to the skin of the individual.

* * * * *